United States Patent [19]

Makino et al.

[11] Patent Number: 4,755,544
[45] Date of Patent: Jul. 5, 1988

[54] SUSTAINED RELEASE PREPARATION

[75] Inventors: Yuji Makino; Hideo Matugi; Yoshiki Suzuki, all of Hino, Japan

[73] Assignee: Teijin Limited, Osaka, Japan

[21] Appl. No.: 870,480

[22] Filed: Jun. 4, 1986

[30] Foreign Application Priority Data

Jun. 4, 1985 [JP] Japan .................................. 60-119692
Jun. 24, 1985 [JP] Japan .................................. 60-135920

[51] Int. Cl.$^4$ .......................... C08L 1/26; A01N 25/26; A01N 25/28; A61F 13/00

[52] U.S. Cl. ......................................... 524/42; 524/43; 524/44; 424/418; 424/419; 424/422; 424/461; 424/462; 424/468; 427/3

[58] Field of Search ...................... 524/42, 43, 44; 424/418, 419, 422, 461, 462, 468, 485, 486; 427/3

[56] References Cited

U.S. PATENT DOCUMENTS

| | | | |
|---|---|---|---|
| 4,126,672 | 11/1978 | Sheth et al. | 424/22 |
| 4,172,055 | 10/1979 | DeMartino | 524/43 |
| 4,252,786 | 2/1981 | Weiss et al. | 424/19 |
| 4,519,801 | 5/1985 | Edgren | 604/892 |
| 4,627,977 | 12/1986 | Gaffar et al. | 424/57 |

FOREIGN PATENT DOCUMENTS 7424615  2/1975  France .
1469133  3/1977  United Kingdom .

*Primary Examiner*—Delbert R. Phillips
*Assistant Examiner*—Nathan M. Nutter
*Attorney, Agent, or Firm*—Sughrue, Mion, Zinn, Macpeak, and Seas

[57] ABSTRACT

A sustained release preparation comprising:
(a) a non-anionic cellulose ether
(b) a methoxyethylene-maleic anhydride copolymer or the hydrolyzate thereof, and
(c) pharmaceutically active agents.

This sustained release preparation can provide the desired sustained-release or dissolution of the pharmaceutically active agents in human organs irrespective of the acidity (i.e., pH conditions) therein.

8 Claims, No Drawings

SUSTAINED RELEASE PREPARATION

BACKGROUND OF THE INVENTION

1. Field of the Invention

The present invention relates to a sustained release preparation. More specifically, it relates to a sustained release preparation in which a combination of (a) a non-anionic cellulose ether and (b) a methoxyethylene-maleic anhydride copolymer or the hydrolyzate thereof is utilized as a sustained-release agent.

2. Description of the Related Art

Techniques for the sustained release of preparations have long been studied, to control the dissolution or release and absorption of medicaments from the preparation in human organs upon administration. For example, it is known in the art that medicaments coated by various film-forming substances or medicaments are included or encapsulated in matrices composed of waxes or polymers. However, generally speaking, these known techniques are disadvantageous in that the production processes are complex and the desired sustained release cannot be satisfactorily attained.

In view of the state of the art as described above, the present inventors investigated the conditions for releasing with certainty medicaments in living bodies, and consequently found that two conditions are necessary for this purpose: (1) that the preparation should have an affinity for the tissue or the organ at the site where the preparation is administered, and (2) that the preparation should easily retain its form without being rapidly dissolved or digested with body fluids (form retentivity). Accordingly, the inventors investigated preparations which are endowed with these two conditions and can be easily prepared.

As the compounds which have heretofore been employed in the cosmetics or pharmaceuticals industries, there are methoxyethylen-maleic anhydride copolymers, which have an excellent affinity with components of living bodies such as mucosa of digestive organs, muscles, and fat tissues, and a large number of application examples of these compounds for pharmaceuticals can be found. It has been reported that the dissolution or release of ephedrine from tablets containing a methoxyethylene-maleic anhydride is delayed (E. Chalhoub et al, Pharm, Ind., 1976, 38 (9), 844–7). Since, however, a methoxyethylene-maleic anhydride is readily soluble in water, when tablets containing a methoxyethylene-maleic anhydride are actually administered to living bodies, the tablets are quickly dissolved, and thus the release of the medicaments cannot be sustained.

Certain kinds of cellulose derivatives, for example, hydroxypropyl cellulose, hydroxypropylmethyl cellulose, methyl cellulose, ethyl cellulose, chitin, and chitosan, all have a high form retentivity through gellation with moisture, and are expected to delay dissolution or release of the coexisting medicaments. U.S. Pat. No. 4,126,672 discloses a process for the production of a sustained release preparation employing hydroxypropylmethyl cellulose. Nevertheless, although these gel forming polymers have a high form retentivity and are preferable for the sustained release of the co-existing medicaments, since they form gels which cannot be rapidly dissolved or digested with body fluids, they lack adhesiveness to or affinity with living bodies. For example, when these gel forming polymers are filled together with medicaments in hard capsules and orally administered into living bodies, they will be rapidly moved into the digestive organs, and thus insufficient absorption will frequently occur.

To the inventors' knowledge, no example of the use of a mixture of a methoxyethylene-maleic anhydride copolymer with a cellulose derivative for a sustained release preparation has yet been reported. U.S. Pat. No. 4,172,055 discloses a mixture of hydroxypropylcellulose with poly (maleic anhydride/alkene-1) as a useful gelling agent, and methoxyethylene-maleic anhydride/alkene-1). The above U.S. patent, however, provides a fluid for hydraulics as an aqueous solution of the above mixture to be used for a drill for use in the excavation of mineral sources such as petroleum, and an investigation has not been made concerning the application thereof for sustained-release preparations.

SUMMARY OF THE INVENTION

Accordingly, the objects of the present invention are to eliminate the above-mentioned disadvantages of the prior art and to provide a controlled sustained release preparation capable of providing the desired sustained release or dissolution of medicaments in human organs irrespective of the acidity (i.e., pH condition) therein.

Other objects and advantages of the present invention will be apparent from the following description.

In accordance with the present invention, there is provided a sustained release preparation comprising:

(a) at least one non-anionic cellulose ether, (b) at least one anionic polymer compound selected from the group consisting of methoxyethylene-maleic anhydride copolymers and the hydrolyzates thereof, and (c) at least one pharmaceutically active agent.

DESCRIPTION OF THE PREFERRED EMBODIMENT

The non-anionic cellulose ethers usable as the component (a) in the present invention may include, for example, hydroxyethyl cellulose, hydroxypropyl cellulose, hydroxypropylmethyl cellulose, methyl cellulose, and ethyl cellulose preferably hydroxypropyl cellulose and hydroxypropylmethyl cellulose.

The anionic polymer compounds usable as the component (b) in the sustained-release preparations according to the present invention are the methoxyethylene-maleic anhydride copolymers and the hydrolyzates thereof. The methoxyethylene-maleic anhydride copolymers usable as a component (b) of the present sustained release preparations are those having the general formula:

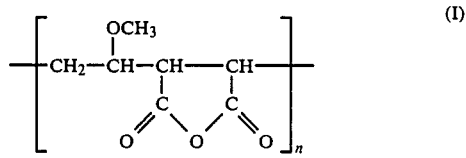

The hydrolyzates of the methoxyethylene-maleic anhydride copolymers having the following general formula:

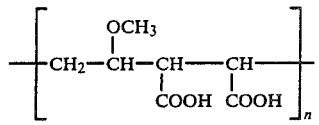

$$\left[ -CH_2-CH-CH-CH- \atop {OCH_3 \atop \phantom{|}} \; {| \atop COOH} \; {| \atop COOH} \right]_n \quad (II)$$

also can be used as a component (b) of the present sustained release preparations. The preferable hydrolyzates are those obtained by hydrolyzing 50% or more, preferably 75% or more, of the maleic anhydride portions to the carboxylic acid groups.

Although there is no limitation to the amount of the component (b) to the component (a) in the sustained release preparations according to the present invention, the preferable formulating weight ratio of the component (b) to the component (a) (i.e., component (b): component (a)) is preferably 95:5 to 10:90, more preferably 80:20 to 20:80, especially preferably 70:30 to 30:70. The formulation of too small an amount of the component (b) tends to decrease the affinity to organ tissues. Conversely, the formulation of too large an amount of the component (b) tends to result in poor form retentivity of the resultant preparations.

The pharmaceutically active agents usable as the component (c) in the present invention can be any of those agents which are generally required to be frequently administered for maintaining the effective blood concentration or effective local content thereof. Typical examples of such pharmaceutically active agents are as follows.

(1) Antipyretic, Analgesic or Antiphlogistic

Mefenamic acid, acemetacin, indomethacin, alclofenac, ibuprofen, tiaramide hydrochloride, ketoprofen, diclofenac sodium, sulindac, naproxen, fenbufen, flurbiprofen, mepirizole, 5-aminosalicylic acid, and the like.

(2) Antiarrhythmics

Acebutolol hydrochloride, alprenolol hydrochloride, indenolol hydrochloride, oxprenolol hydrochloride, carteolol hydrochloride, propranolol hydrochloride, pindolol, disopyramide, and the like.

(3) Hypotensors

Clonidine hydrochloride, prazosin hydrochloride, captopril, metoprolol tartrate, methyldopa, betanidine sulfate, and the like.

(4) Vasodilator

Etafenone hydrochloride, oxyfedrine hydrochloride, Carbochromen hydrochloride, dilazep dihydrochloride, diltiazem hydrochloride, trimetazidine hydrochloride, verapamil hydrochloride, dipyridamole, isosorbide dinitrate, trapidil, nicorandil, nifedipine, inositol hexanicotinate, isoxsuprine hydrochloride, nicametate citrate, cyclandelate, cinnarizine, and the like.

(5) Antiarteriosclerotics

Clofibrate, simfibrate, elastase, systerol, nicomol, and the like.

(6) Agents for Circulating Systems

Nicardipine hydrochloride, nimodiphine hydrochloride, meclofenoxate hydrochloride, cytochrome C, ifenprodil tartrate, tocopherol nicotinate, pentoxiflyline, and the like.

(7) Antitussive expectorants

Clorprenaline hydrochloride, pirbuterol hydrochloride, bitolterol mesilate, salbutanol hemisulfate, terbutaline sulfate, hexoprenaline sulfate, dimemorfan phosphate, ambroxal hydrochloride, L-ethylcystine hydrochloride, trimetoquinol hydrochloride, bromhexine hydrochloride, theophylline, tranilast, and the like.

(8) Ulcer Preventives

Aceglutamide aluminum, L-glutamin, P-(trans-4-aminomethylcyclohexanecarbonyl)-phenylpropionic acid hydrochloride, cetraxate hydrochloride, pirenzepine hydrochloride, gefarnate, cimetidine, glycopyrronium bromide, sulpiride, and prostaglandins such as 17,20-dimethyl-6-oxoprostaglandin $E_1$ methyl ester, 6-oxoprostaglandin $E_1$, 15-methyl-prostaglandin $E_2$, 16-methyl-16-hydroxy-15-depheroxy-prostaglandin $E_1$ methyl ester, 7-thinaprostaglanding $E_1$ methylester, 17,20-dimethyl-7-thiaprostaglandin $E_1$ methyl ester, isocarbacyclins, and the like.

(9) Enzyme Preparations

Chymotrypsin, streptokinase, lysozyme chloride, seaprose, serrapeptase, pronase, bromelains, montease, and the like.

(10) Antimalignant Agents

Methotrexate, carboquone, carmofur, tegaful, 6-mercaptopurine, fluorouracil, and the like.

(11) Chemotherapeutic Agents

Oxacillin, pheneticillin potassium, amoxicilline, ampicillin, cefalexin, cefradin, and the like.

(12) Antiphlogistic Steroid Agents

Hydrocortisone, prednisolone, triamcinolone, triamcinolone acetanide, dexamethasone, betamethasone, and the like.

(13) Antihistamine Agents

Diphenyldramine hydrochloride, chlorpheniramine maleate, and the like.

(14) Local Anesthetic Agents

Benzocaine and the like.

(15) Mouth Disinfection Agents

Chlorohexidine hydrochloride, hexylresorcin, etacrysin, and the like.

(16) Smooth Muscle Relaxants

Flavoxate hydrochloride and the like.

(17) Bone Metabolism Controlling Agents $1\alpha$-Hydroxyvitamin $D_3$, $1\alpha$, 24-dihydroxyvitamin $D_3$, $1\alpha$, 25-dihydroxyvitamin $D_3$, and the like.

According to the present invention, the desired sustained release preparatiosn can be prepared by mixing the above-mentioned components (a), (b) and (c), and any optional components, by any conventional method. Before mixing these components, each component is preferably ground or pulverized to a uniform fine powder having a particle size of, for example, about 5 to 500 $\mu$m, more preferably, 10 to 200 $\mu$m. The grinding can be carried out by any conventional grinding machine such as a centrifugal grinder. Furthermore, the grinding may be carried out after mixing the above-mentioned three components. The amount of the pharmaceutically active agents to be formulated into the present sustained release preparation can be varied depending upon, for example, the type of the pharmaceutically active agents and, therefore, may be optionally selected based on, for example, the intensity of their activities.

The sustained-release preparations according to the present invention may be orally, intraorally, intranasally, or locally administered. Alternatively, the present sustained release preparations may be directly applied to the inside of the tissue. The present sustained release preparations may be in the form of, for example, tablets, granules, grains, powders, dental cones, films, or hard capsules.

These preparations can be prepared by any conventional manner. For example, the resultant mixture may be directly or optionally mixed with any conventional ingredients such as foaming agents, lubricants, binders, colorants, and/or flavors prepared to form powders. Examples of foaming agents are sodium bicarbonate and the like. Examples of such lubricants are talc, stearic acid and the salts thereof, and waxes. Examples of binders are starch, dextrin, tragaconth, gelatin, polyvinylpyrrolidone, hydroxypropylcellulose, and polyvinyl alcohol. Examples of the colorants are tar type dyes such as Sunset Yellow. These ingredients may be incorporated into the preparations, unless such incorporation will adversely affect the sustained-release property thereof.

The present sustained release preparations may be prepared in the form of tablets by direct compression molding of a uniform mixture of the compounds (a), (b), and (c), and optional ingredients such as foaming agents, lubricants, binders, or colorants. Furthermore, the mixture may be granulated by any conventional method to form granules. The resultant granules may be further ground to form powders.

These preparations may be administered to human organs in any conventional manner so that the activities of the pharmaceutically active agents contained therein can be sufficiently effected. For example, antipyretic, analgesic, or antiphlogistics, antiarrhythmics, hypotensors, vasodilators, antiarteriosclerotics, agents for circulating systems, antitussive expectorants, ulcer preventives, enzyme preparations, antimalignant agents, chemotherapeutic agents, antiphlogistic steroid agents, antihistamine agents, and the like may be perorally administered. Antiarrhythmics, hypotensors, vasodilators, antiarteriosclerotics, agents for circulating systems, antiphlogistic steroid agents, local anesthetic agents, and mouth disinfection agents may be locally administered intraorally or intranasally. Further, antimalignant agents may be directly applied to the inside of the infected tissue.

According to the present invention, pharmaceutically active agents which, in general must be frequently administered to maintain the effective blood concentraion or effective local concentration thereof, can be advantageously incorporated into the present sustained release preparations. Thus, the desired sustained release of these pharmaceutically active agents can be attained and the administration frequency thereof can be remarkably decreased.

EXAMPLES

The present invention will now be further illustrated in detail by, but is by no means limited to, the following Examples, wherein "parts" are all by weight unless otherwise noted.

Example 1

According to the process of the present invention, 42.25 parts of a hydrolyzate of methoxyethylene-maleic anhydride copolymer (95% hydrolyzate: Gantrez S-95 if GAF Co.), 42.25 parts of hydroxypropyl cellulose, 15.0 parts of nifedipine and 0.5 parts of magnesium stearate were thoroughly mixed to obtain a powdery composition, and tablets were prepared from this composition in a conventional manner (one tablet=200 mg). The dissolution test was conducted according to the second method of the dissolution test procedure (the Paddle method) defined in the Pharmacopoeia of Japan (Tenth edition), using the No. 1 test solution (pH=1.2).

The tablets were prepared by a KBr tablet molding machine and a hydraulic press for an infrared absorption spectral analysis under a compresion pressure of 100 kg for 30 seconds. Thus, flat plate tablets having a diameter of 13 mm were formed. The test solution was sampled with the elapse of time, and the amounts of nifedipin dissolved were spectrophotometrically determined and the dissolution rate was calculated from the concentration. At the same time, as controls, tablets comprising 42.25 parts of microcrystalline cellulose, 42.25 parts of lactose, 15.0 parts of nifedipine, and 0.5 parts of magnesium stearate (Control 1); tablets comprising 84.5 parts of a hydrolyzate of a methoxyethylene-maleic anhydride copolymer, 15.0 parts of nifedipine, and 0.5 parts of magnesium stearate (Control 2); and tablets comprising 84.5 parts of hydroxypropyl cellulose, 15.0 parts of nifedipine, and 0.5 parts of magnesium stearate (Control 3) were also subjected to dissolution tests in the same manner as mentioned above.

The results are as shown in Table 1.

TABLE 1

| Tablet | Time | | | | |
|---|---|---|---|---|---|
| | 5 min | 15 min | 30 min | 1 hr | 3 hr |
| Example 1 | — | — | 5 | 11 | 23 |
| Control 1 | 65 | 97 | 100 | — | — |
| Control 2 | — | 8 | 17 | 30 | 59 |
| Control 3 | — | 5 | 12 | 19 | 40 |

As clear from the results shown in Table 1, the dissolution of Example 1 is delayed as compared with Controls 1 to 3.

Example 2

The tablets prepared in Example 1 and the tablets of Controls 2 and 3 in Example 1 were administered, with 50 ml of water to healthy human volunteers and, after administration, blood was sampled after a lapse of time and the nifedipine level in blood was measured by ECD type gas chromatography. The results are shown in Table 2.

As clear from the results shown in Table 2, Example 1 was longer sustained as compared with Controls 2 and 3, even when actually administered to human beings.

TABLE 2

| Volunteer | Sex | Body weight | Medicament | Nifedipine concentration in blood (ng/ml) | | | | | |
|---|---|---|---|---|---|---|---|---|---|
| | | | | 30 min | 1 hr | 2 hr | 8 hr | 16 hr | 24 hr |
| A | Male | 58 kg | Example 1 | 10 | 28 | 39 | 41 | 25 | 5 |
| B | Male | 61 kg | Example 1 | 7 | 25 | 52 | 36 | 19 | 3 |
| C | Male | 55 kg | Control 2 | 15 | 26 | 30 | 12 | 4 | — |
| D | Male | 73 kg | Control 2 | 12 | 40 | 27 | 18 | 6 | — |
| E | Male | 64 kg | Control 3 | 18 | 42 | 20 | 9 | 1 | — |
| F | Male | 59 kg | Control 3 | 25 | 27 | 31 | 14 | 3 | — |

Example 3

According to the process of the present invention, 43.5 parts of a hydrolyzate of methoxymethylene-maleic anhydride copolymer (95% hydrolyzate: Gantrez S-95 of GAF Co.), 43.5 parts of hydroxypropyl cellulose, 12.5 parts of indomethacin, and 0.5 parts of magnesium stearate were thoroughly mixed to obtain a powdery composition, and tablets were prepared from this composition in a conventional manner (one tablet=200 mg). The dissolution test was conducted according to the second method of the dissolution test procedure (the Paddle method) defined in the Pharmacopoeia of Japan (Tenth edition), using the No. 1 test solution (pH=1.2).

The tablets were prepared by a KBr tablet molding machine and a hydraulic press for an infrared absorption spectral analysis under a compression pressure of 100 kg for 30 seconds. This, flat plate tablets having a diameter of 13 mm were formed. The test solution was sampled after an elapse of time, and the amounts of indomethacin dissolved were spectrophotometrically determined and the dissolution rate was calculated from the concentration. At the same time, as controls, tablets comprising 43.5 parts of microcrystalline cellulose, 43.5 parts of lactose, 12.5 parts of indomethacin, and 0.5 parts of magnesium stearate (Control 4); tablets comprising 87.0 parts of a hydrolyzate of a methoxyethylene-maleic anhydride copolymer, 12.5 parts of indomethacin and 0.5 parts by weight of magnesium stearate (Control 5); and tablets comprising 87.0 parts of hydroxypropyl cellulose, 12.5 parts of indomethacin, and 0.5 parts of magnesium stearate (Control 6) were also subjected to dissolution tests in the same manner as mentioned above.

The results are as shown in Table 3.

TABLE 3

| Tablet | Time | | | | |
|---|---|---|---|---|---|
| | 5 min | 15 min | 30 min | 1 hr | 3 hr |
| Example 3 | — | — | 6 | 10 | 24 |
| Control 4 | 71 | 98 | 99 | — | — |
| Control 5 | — | 10 | 21 | 36 | 59 |
| Control 6 | — | 7 | 18 | 29 | 48 |

Example 4

In place of the hydroxypropyl cellulose of Example 3, hydroxy propylmethyl cellulose was used to prepare a tablet of indomethacin, and a dissolution test was conducted in the same manner as in Example 3.

The results are shown in Table 4.

TABLE 4

| Example | Composition | | | | Dissolution rate | | | | |
|---|---|---|---|---|---|---|---|---|---|
| | | | | | 5 min | 15 min | 30 min | 1 hr | 3 hr |
| 4 | Hydrolyzate of methoxyethylene-maleic anhydride copolymer (43.5 parts) | Hydroxypropylmethyl cellulose (43.5 parts) | Indomethacin (12.5 parts) | Magnesium stearate (0.5 parts) | — | — | 10 | 18 | 29 |

Example 5

Tablets each having a weight of 200 mg comprising 42.5 parts of a hydrolyzate of a methoxyethylene-maleic anhydride copolymer, 42 parts of hydroxypropyl celulose, 15 parts of propranolol hydrochloride, and 0.5 parts of magnesium stearate were prepared in the same manner as in Example 1.

Example 6

Tablets each having a weight of 40 mg comprising 50.0 parts of a hydrolyzate of a methoxyethylene-maleic anhydride copolymer, 49.5 parts of hydroxypropyl cellulose, 0.01 part of triamcinolone acetonide, and 0.5 parts of magnesium stearate were prepared in the same manner as in Example 1.

Example 7

Tablets comprising 42.25 parts of methoxymethylene-maleic anhydride copolymer (Gantrez AN-149 of GAF Co.), 42.25 parts of hydroxypropyl cellulose, 15.0 parts of nifedipine, and 0.5 parts of magnesium stearate were prepared (one tablet=200 mg) according to the process of the present invention, and the dissolution test was conducted according to the second method of the dissolution test procedure (the Paddle method) defined in the Pharmacopoeia of Japan (Tenth edition), using the No. 1 test solution (pH=1.2).

The tablets were prepared by a KBr tablet molding machine and a hydraulic press for an infrared adsorption spectral analysis under a compression pressure of 100 kg for 30 seconds. Thus, flat plate tablets having a diameter of 13 mm were formed. The test solution was sampled after an elapse of time, and the amounts of nifedipin dissolved were spectrophotometrically determined and the dissolution rate was calculated from the concentration. At the same time, as controls, tablets comprising 42.25 parts of microcrystalline cellulose, 42.25 parts of lactose, 15.0 parts of nifedipine, and 0.5 parts of magnesium stearate (Control 7); tablets comprising 84.5 parts of a methoxyethylene-maleic anhydride copolymer, 15.0 parts of nifedipine, and 0.5 parts by weight of magnesium stearate (Control 8); and tablets comprsing 84.5 parts of hydroxypropyl cellulose, 15.0 parts of nifedipine, and 0.5 parts of magnesium stearate (Control 9) were also subjected to dissolution tests in the same manner as mentioned above.

The results are as shown in Table 5.

TABLE 5

| Tablet | Time | | | | |
| --- | --- | --- | --- | --- | --- |
| | 5 min | 15 min | 30 min | 1 hr | 3 hr |
| Example 7 | — | — | 8 | 13 | 30 |
| Control 7 | 65 | 97 | 100 | — | — |
| Control 8 | — | 10 | 21 | 33 | 61 |
| Control 9 | — | 5 | 12 | 19 | 40 |

As clear from the results shown in Table 5, the dissolution of Example 7 is delayed compared with Controls 7 to 9.

Example 8

The tablets prepared in Example 7 and the tablets of Controls 8 and 9 in Example 7 were administered, with 50 ml of water, to healthy human volunteers and, after administration, blood was sampled after a lapse of time and the nifedipine level in the blood was measured by ECD type gas chromatography. The results are shown in Table 6.

As clear from the results shown in Table 5, Example 7 was longer sustained as compared with Controls 8 and 9, even when actually administered to human beings.

TABLE 6

| Volunteer | Sex | Body weight | Medicament | Nifedipine concentration in blood (ng/ml) | | | | | |
| --- | --- | --- | --- | --- | --- | --- | --- | --- | --- |
| | | | | 30 min | 1 hr | 2 hr | 8 hr | 16 hr | 24 hr |
| A | Male | 58 kg | Example 7 | 10 | 30 | 48 | 39 | 18 | 25 |
| B | Male | 61 kg | Example 7 | 11 | 27 | 50 | 33 | 21 | 23 |
| C | Male | 55 kg | Control 8 | 14 | 30 | 31 | 10 | 5 | — |
| D | Male | 73 kg | Control 8 | 12 | 29 | 35 | 13 | 5 | — |
| E | Male | 64 kg | Control 9 | 18 | 42 | 20 | 9 | 1 | — |
| F | Male | 59 kg | Control 9 | 25 | 27 | 31 | 14 | 3 | — |

100 kg for 30 seconds. Thus, flat plate tablets having a diameter of 13 mm were formed. The test solution was sampled after an elapse of time, and the amounts of indomethacin dissolved were spectrophotometrically determined and the dissolution rate was calculated from the concentration. At the same time, as controls, tablets comprising 43.5 parts of microcrystalline cellulose, 43.5 parts of lactose, 12.5 parts of indomethacin, and 0.5 parts of magnesium stearate (Control 10); tablets comprising 87.0 parts of a methoxyethylene-maleic anhydride copolymer, 12.5 parts of weight of indomethacin, and 0.5 parts of magnesium stearate (Control 11); and tablets comprising 87.0 parts of hydroxypropyl cellulose, 12.5 parts by weight of indomethacin, and 0.5 parts of magnesium stearate (Control 12) were also subjected to dissolution tests in the same manner as mentioned above.

The results are shown in Table 6.

TABLE 6

| Tablet | Time | | | | |
| --- | --- | --- | --- | --- | --- |
| | 5 min | 15 min | 30 min | 1 hr | 3 hr |
| Example 9 | — | — | 10 | 13 | 29 |
| Control 10 | 71 | 98 | 99 | — | — |
| Control 11 | — | 11 | 25 | 43 | 66 |
| Control 12 | — | 7 | 18 | 29 | 48 |

Example 10

In place of hydroxypropyl cellulose in Example 9, the cellulose derivatives as indicated in Table 7 were used to prepare tablets of indomethacin, and dissolution tests were conducted in the same manner as in Example 9.

The result are shown in Table 7.

TABLE 7

| Example | Composition | | | | Dissolution rate | | | | |
| --- | --- | --- | --- | --- | --- | --- | --- | --- | --- |
| | | | | | 5 min | 15 min | 30 min | 1 hr | 3 hr |
| 10 | Hydrolyzate of methoxyethylene-maleic anhydride copolymer (43.5 parts) | Hydroxypropylmethyl cellulose (43.5 parts) | Indomethacin (12.5 parts) | Magnesium stearate (0.5 parts) | — | — | 9 | 20 | 29 |

Example 9

Tablets comprising 43.5 parts of methoxymethylene-maleic anhydride copolymer (Gantrez AN-169 of GAF Co.), 43.5 parts of hydroxypropyl cellulose, 12.5 parts of indomethacin, and 0.5 parts of magnesium stearate were prepared (one tablet=200 mg) according to the process of the present invention, and the dissolution test was conducted according to the second method of the dissolution test procedure (the Paddle method) defined in the Pharmacopoeia of Japan (Tenth edition), using the No. 1 test solution (pH=1.2).

The tablets were prepared by a KBr tablet molding machine and a hydraulic press for an infrared adsorption spectral analysis under a compression pressure of Example 11

Tablets each having a weight of 200 mg comprising 42.5 parts by weight of a methoxyethylene-maleic anhydride copolymer (Gantrez AN-119 of GAF Co.), 42 parts of hydroxypropyl cellulose, 15 parts of propranolol hydrochloride, and 0.5 parts of magnesium stearate were prepared in the same manner as in Example 7.

Example 12

Tablets each having a weight of 40 mg comprising 50.0 parts of a methoxyethylene-maleic anhydride copolymer (Gantrez AN-179 of GAF Co.), 49.5 parts of hydroxypropyl cellulose, 0.01 part of triamcinolone acetonide, and 0.5 parts of magnesium stearate were prepared in the same manner as in Example 7.

Example 13

Tablets each having a weight of 500 mg comprising 39.9 parts by weight of a methoxyethylene-maleic anhydride copolymer (Gantrez AN-119 of GAF Co.), 39.9 parts by weight of hydroxypropylmethyl cellulose, 20.0 parts by weight of 5-aminosalicylic acid, and 0.5 parts by weight of magnesium stearate were prepared in the same manner as in Example 7.

We claim:

1. A sustained release preparation comprising:
   (a) at least one non-anionic cellulose ether,
   (b) at least one anionic polymer compound selected from the group consisting of methoxyethylene-maleic anhydride copolymers and the hydrolyzates thereof, and
   (c) at least one pharmaceutically active agent.
2. A sustained release preparation as claimed in claim 1, wherein said non-anionic cellulose ethers are hydroxypropyl cellulose, hydroxypropylmethyl cellulose, methyl cellulose, and ethyl cellulose.
3. A sustained release preparation as claimed in claim 1, wherein the hydrolyzate of the methoxyethylene-maleic anhydride copolymer is the methoxyethylene-maleic anhydride copolymer of which at least 50% of the maleic anhydride moiety is hydrolyzed.
4. A sustained release preparation as claimed in claim 1, wherein the weight ratio of the component (b) to the component (a) is 95:5 to 10:90.
5. A sustained release preparation as claimed in claim 1, wherein the pharmaceutically active agent is at least one member selected from the group consisting of antipyretic, analgesic, or antiphlogistics, antiarrhythmics, hypotensors, vasodilators antiarteriosclerotics, agents for circulatory systems, antitussive expectorants, ulcer preventives, enzyme preparations, antimalignants, chemothoerapeutic agents, antiphlogistic steroid agents, antihistamine agents, local anesthetic agents, mouth disinfection agents, and bone metabolism controlling agents.
6. A sustained release preparation as claimed in claim 1, which is the form of tablets, granules, grains, powders, dental cones, films, or hard capsules.
7. A method for administering a sustained release preparation according to claim 1 whereby the pharmaceutically active agent contained therein is gradually released.
8. A method as claimed in claim 7, wherein the preparation is orally, intraorally or intranasally administered.

* * * * *